United States Patent
Sadovsky et al.

(10) Patent No.: US 10,376,607 B2
(45) Date of Patent: Aug. 13, 2019

(54) NEUTRALIZATION OF ODORS

(71) Applicant: SADOVSKY LTD., Ashkelon (IL)

(72) Inventors: Shmuel Sadovsky, Ashkelon (IL); Uri Bach, Efrat (IL)

(73) Assignee: Sadovsky Ltd., Ashkelon (IL)

(*) Notice: Subject to any disclaimer, the term of this patent is extended or adjusted under 35 U.S.C. 154(b) by 9 days.

(21) Appl. No.: 15/533,538

(22) PCT Filed: Dec. 7, 2015

(86) PCT No.: PCT/IL2015/051186
§ 371 (c)(1),
(2) Date: Jun. 6, 2017

(87) PCT Pub. No.: WO2016/092541
PCT Pub. Date: Jun. 16, 2016

(65) Prior Publication Data
US 2018/0264158 A1  Sep. 20, 2018

(30) Foreign Application Priority Data
Dec. 7, 2014 (IL) .......................................... 236099

(51) Int. Cl.
| A61L 9/013 | (2006.01) |
| A61L 9/12 | (2006.01) |
| A61L 9/14 | (2006.01) |
| A61L 9/012 | (2006.01) |
| A61L 9/05 | (2006.01) |
| A61L 2/18 | (2006.01) |

(52) U.S. Cl.
CPC .................... *A61L 9/14* (2013.01); *A61L 2/18* (2013.01); *A61L 9/012* (2013.01); *A61L 9/05* (2013.01); *A61L 2209/21* (2013.01); *C02F 2303/02* (2013.01)

(58) Field of Classification Search
None
See application file for complete search history.

(56) References Cited

U.S. PATENT DOCUMENTS

| 3,824,633 A | 7/1974 | Van Vlahakis |
| 2003/0097936 A1* | 5/2003 | Maleeny ............... A61L 9/012 95/285 |
| 2003/0104969 A1 | 6/2003 | Caswell et al. |
| 2004/0082495 A1 | 4/2004 | Maleeny et al. |
| 2004/0101459 A1 | 5/2004 | Schur |
| 2006/0201145 A1* | 9/2006 | Brady ............... B01D 53/92 60/310 |
| 2006/0216365 A1 | 9/2006 | Massif et al. |
| 2007/0166341 A1 | 7/2007 | Nakatsu et al. |
| 2009/0175758 A1 | 7/2009 | Burrows et al. |
| 2009/0235443 A1 | 9/2009 | Arora et al. |
| 2009/0324663 A1 | 12/2009 | Legendre et al. |
| 2011/0318296 A1* | 12/2011 | Braun ............... A61L 9/05 424/76.1 |
| 2012/0097754 A1 | 4/2012 | Vlad et al. |
| 2015/0111809 A1 | 4/2015 | Marini et al. |

FOREIGN PATENT DOCUMENTS

| JP | 6007417 A | 1/1994 |
| JP | 7031669 A | 2/1995 |
| JP | 7171209 A | 7/1995 |
| JP | 2000069944 A | 3/2000 |
| WO | 2005063945 A1 | 7/2005 |
| WO | 2009131748 A1 | 10/2009 |
| WO | 2015099640 A1 | 7/2015 |

OTHER PUBLICATIONS

"How to Kill Mosquito Larvae in Standing Water With Household Products" https://www.hunker.com/13406092/natural-flea-tick-remedy; accessed Dec. 6, 2018; articles dated Aug. 28, 2017 (Year: 2017).*
Technical Data Sheet for TERGITOL™ NP-10 Surfactant from Dow, accessed Dec. 6, 2018 (Year: 2018).*
Technical Data Sheet for TERGITOL™ NP-6 Surfactant from Dow, accessed Dec. 6, 2018 (Year: 2018).*
Kadarohman, Asep, et al. "A potential study on clove oil, eugenol and eugenyl acetate as diesel fuel bio-additives and their performance on one cylinder engine." Transport 25.1 (2010): 66-76. (Year: 2010).*

* cited by examiner

*Primary Examiner* — Nissa M Westerberg
(74) *Attorney, Agent, or Firm* — McAndrews, Held & Malloy, Ltd.

(57) ABSTRACT

The present disclosure provides compositions comprising at least one eugenol-containing odor neutralizing agent and at least one film forming agent for treating, reducing or neutralizing malodors.

17 Claims, No Drawings

NEUTRALIZATION OF ODORS

This application is filed pursuant to 35 U.S.C. 371 as a U.S. National Phase application of International Patent Application No. PCT/IL2015/051186, which was filed Dec. 7, 2015, claiming the benefit of priority to Israel Patent Application No. 236099, which was filed on Sep. Dec. 7, 2014. The content of each of the aforementioned patent applications is incorporated herein by reference in its entirety.

TECHNOLOGICAL FIELD

The invention relates to a composition and method for neutralization of odors.

BACKGROUND

The treatment of malodors in domestic and industrial areas has attracted some attention in the recent decades. Most solutions available in the market today address the issue of masking or eliminating malodors in the gaseous phase by applying aerosols or sprays which contain fragrances, of synthetic or natural source [1], or neutralizing chemical agents [2] in the gas phase. Such solutions do not address the problem of treatment of wastewater in the liquid phase in order to eliminate malodorous which are associated with volatile compounds originating from within the wastewater.

For domestic uses, standard containers allowing the release of a measured amount of disinfecting and surface-active compounds are typically used [3]. Although providing a disinfecting effect and often comprising fragrance components, these products do not treat the volatile compounds causing malodors, but are rather used for masking the malodors once the volatile compounds have been released from the water into the gas phase.

Therefore, there exists a need for odor-neutralizing compositions that reduce the content of malodorous volatile compounds above aqueous reservoirs by treatment of said volatile compounds in the water phase, as well as those present in the gaseous phase above the water. Preferably, such compositions are required to be also environmentally-friendly and of low cost.

REFERENCES

References considered to be relevant as background to the presently disclosed subject matter are listed below:
[1] JP7031669
[2] WO 2005/063945
[3] U.S. Pat. No. 3,824,633

Acknowledgement of the above references herein is not to be inferred as meaning that these are in any way relevant to the patentability of the presently disclosed subject matter.

SUMMARY OF THE INVENTION

The inventors of the present invention have found that compositions comprising certain essential oils provide satisfactory odor neutralization without the need to employ environmentally unfriendly materials. The odor neutralizing effect may be obtained by using relatively small quantities of a neutralizing composition, either when applied as a spray above a liquid phase to be treated (for example, by spraying) or when applied directly into the liquid phase.

In one of its aspects, the invention provides an odor neutralizing composition comprising at least one eugenol-containing odor neutralizing agent and at least one film forming agent.

The term "odor neutralization" or any lingual variations thereof, refers to reducing, minimizing, or eliminating malodors from a gas phase, which may, by some embodiments, be present above an aqueous phase, e.g., in which the source of the malodors is present or contained (not necessarily in a dissolved state). Such malodors are often caused by release of volatile sulphur-based or nitrogen-containing compounds from the aqueous phase into the gas phase. Without wishing to be bound by theory, the active components of the composition of the invention, i.e. the odor neutralizing agent, associates physically with the volatile compounds in the aqueous phase (typically be forming micelles), thereby reducing their volatilization. In addition, the neutralizing agent may react chemically with the volatile compounds, thereby preventing their volatilization into the gaseous phase. Therefore, neutralization also refers to a reduction in the concentration of these volatile compounds, in the gas phase, to a level below the scent-detection limit (threshold) of the human nose.

The eugenol-containing neutralizing agent used in compositions of the invention may be any type of natural or synthetic composition of matter comprising eugenol. In some embodiments, the neutralizing agent is eugenol (4-Allyl-2-methoxyphenol) in pure (neat) form.

In other embodiments, the at least one odor neutralizing agent is at least one eugenol-containing "essential oil", i.e. a hydrophobic liquid containing volatile aroma compounds, usually obtained from vegetative origin. Such essential oils may be obtained by any method known in the art, such as distillation, solvent extraction, expression, etc. Without wishing to be bound by theory, once in the aqueous phase to be treated, the essential oil forms micellar structures, encapsulating the volatile compounds, thereby drastically reducing their volatility.

In some embodiments, said at least one eugenol-containing essential oil is selected from *Myrtacea* oils, *Artemicia* oils, *Cinnamomum* oils, *Myristica* oils, *Ocimum* oils, *Illicium* oils, and *Melissa* oils. In other embodiments, the at least one essential oil is selected from *Syzygium aromaticum* oil (clove oil), *Arthemisia absinthum* oil (wormwood oil), *Cinnamomum cassia* oil (*C. aromaticum* oil), *Cinnamomum verum* oil (true cinnamon oil), *Cinnamomum tamala* oil (Indian bay leaf oil), *Myristica fragrans* oil (nutmeg oil), *Ocimum basilicum* oil (sweet basil oil), *Ocimum gratissimum* oil (African basil oil), *Ocimum tenuiflorum* oil (tulsi oil), *Ocimum sanctum* oil (holy basil oil), *Illicium anisatum* oil (Japanese star anise oil), *Melissa officinalis* oil (lemon balm oil), *Anethum graveolens* oil (Dill oil), *Pimenta racemosa* oil, *Vanilla fragrans* oil, and *Apium graveolens* oil (celery oil).

In some embodiments, said at least one essential oil is a clove-based essential oil.

According to some embodiments, the composition comprises said at least one odor neutralizing agent in a content of between about 1 and 20 wt % of the composition, i.e. 1,2, 3, 4, 5, 6, 7, 8, 9, 10, 11, 12, 13, 14, 15, 16, 17, 18, 19 or 20 wt % of the composition. In such embodiments, the content of the odor neutralizing agent may be between 1 and 15 wt % of the composition. In other such embodiments, the content of the odor neutralizing agent may be between 5 and 15 wt % of the composition The term film-forming agent is meant to encompass compounds (or mixtures of compounds) which function to form a film onto the surface of the liquid to be treated (e.g. water), thereby forming a barrier between the liquid and the gaseous environment above it. The film-forming agent forms a molecular or bi-molecular layer at the surface of the liquid, thereby functioning as a substantially impermeable barrier, preventing transport of volatile species from the liquid phase to the gaseous phase.

In some embodiments the film-forming agent is MLO (mosquito larvicidal oil). The MLO may comprise at least nonylphenol ethoxylate NP4, sorbitan oleate, silicon oil and hydrotreated light naphthenic and heavy paraffins.

According to some embodiments, the composition comprises said film-forming agent in a content of at least 1 wt %, typically between about 1 and 30 wt % of the composition. In other embodiments, the film-forming agent in a content of between about 2 and 25 wt % of the composition.

In some embodiments, the composition may further comprise at least one viscosity-controlling agent. The viscosity-controlling agent provides a desired viscosity to the composition. In accordance with some embodiments, the at least one viscosity-controlling agent is selected from acrylate/acrylomethyltaurate copolymers, hydroxylated acrylate/acrylomethyltaurate copolymers, polyacrylates, polyisobutenes, and polysorbates.

In such embodiments, the at least one viscosity-controlling agent may be hydroxyethyl-acrylate/sodium-acryloyldimethyltaurate copolymer (Sepinov-EMT™).

In other embodiments, the at least one viscosity-controlling agent may comprise at least octyldodecanol, octyldodecyl xyloside, PEG 30 dipolyhydroxy stearate or any combination thereof (Easynov™)

According to some embodiments, the composition comprises said at least one viscosity-controlling agent in a content of between about 0.5 and 1.5 wt % of the composition. In some other embodiments, the content of the viscosity-controlling agent may be between about 0.5 and 1 wt % of the composition.

According to some embodiments, the composition may further comprise at least one additive.

By some embodiments, the at least one additive may be selected from alkylphenol ethoxylates, fatty alcohols, alcohol ethoxylates, alcohol ethoxysulfates, polyoxyethylene glycol alkyl ethers, polyoxypropylene glycol alkyl ethers, glucoside alkyl ethers, glycerol alkyl esters polyoxyethylene glycol octylphenol ethers (Triton X-100), polyoxyethylene glycol sorbitan alkyl esters (polysorbate), sorbitan alkyl esters, cocamide MEA/DEA, block copolymers of polyethylene glycol and polypropylene glycol (poloxamers). According to other embodiments, the additive is selected from nonylphenol ethoxylate (NP10) or $C_{14}$-$C_{18}$ alcohol ethoxylate. In some other embodiments, the additive is nonylphenol ethoxylate (NP10). In yet other embodiments, the additive is $C_{14}$-$C_{18}$ alcohol ethoxylate.

By some embodiments, the additive is an emulsifier. The term emulsifier denotes surfactant compounds, encompassing any agent that is capable of lowering the surface tension of a liquid, allowing for the formation of a homogeneous mixture of at least one type of liquid with at least one other type of liquid (i.e. to form a mixture of the essential oil and water).

Without wishing to be bound by theory, the emulsifier molecules coat the surface of the oil (i.e. eugenol) droplets, creating a steric hindrance and/or electrostatic repulsion between the coated droplets, thereby facilitating the droplets dispersion in the aqueous medium. Such emulsifiers may thus be selected from an electrostatic stabilizer, a steric stabilizer, and an electrosteric stabilizer. The emulsifiers may be surface-active materials, usually having at least one voluminous pendent group, electrostatic charge or being of high polarity.

In some embodiments, the at least one emulsifier is typically a non-ionic surfactant, which may be selected from alkylphenol ethoxylates, fatty alcohols, alcohol ethoxylates, alcohol ethoxysulfates, polyoxyethylene glycol alkyl ethers, polyoxypropylene glycol alkyl ethers, glucoside alkyl ethers, glycerol alkyl esters polyoxyethylene glycol octylphenol ethers (Triton X-100), polyoxyethylene glycol sorbitan alkyl esters (polysorbate), sorbitan alkyl esters, cocamide MEA/DEA, block copolymers of polyethylene glycol and polypropylene glycol (poloxamers).

In some embodiments, said at least one additive is an emulsifier which is selected from nonylphenol ethoxylate (NP10) and $C_{14}$-$C_{18}$ alcohol ethoxylate.

In some embodiments, the composition is in a liquid form. In such embodiments, the at least one additive is an emulsifier, which may be present in a content of between about 3 and 35 wt % of the composition. According to such embodiments, the at least one emulsifier is nonylphenol ethoxylate (NP10) and the at least one eugenol-containing odor neutralizing agent is eugenol.

In some embodiments, the emulsifier in present in a content of between about 3 and 30 wt %, between about 3 and 25 wt % or even between about 3 and 20 wt % of the composition. In other embodiments, the emulsifier in present in a content of between about 4 and 35 wt %, between about 5 and 35 wt % or even between about 7 and 35 wt % of the composition.

When in liquid form, the composition of the invention may also comprise water, which in some embodiments may be in a content of between about 50 and 90 wt % of the entire composition. In other embodiments the liquid composition may comprise water in a content of between about 55 and 90 wt %, between about 60 and 90 wt %, or even between about 65 and 90 wt % of the entire composition. In some other embodiments, the liquid composition may comprise water in a content of between about 50 and 85 wt %, between about 50 and 80 wt %, or even between about 50 and 75 wt % of the entire composition.

Liquid compositions of the invention may be in a form selected from an emulsion, a liquid and a paste, characterized by a viscosity of between about 200 and 6500 cps (centipoises). Emulsion is meant to denote thermodynamically stable liquid systems, self-assembled into droplets or other structures of the essential oil and water in the presence of surfactants (e.g. the emulsifier). The emulsion may be one as known in the art, such as micro-emulsion, mini-emulsion, nano-emulsion, a double emulsion, lyotropic liquid crystals, or any combination thereof or any other type of micro- or nanostructured liquid.

According to some embodiments, the composition may further comprise a thickener, which may optionally be selected from glyceryl caprylate, glyceryl caprate and combinations thereof. The thickener is often added to composition, typically liquid compositions, is order to obtain the desired viscosity. Liquid compositions of the invention may be formulated for application by spraying or aerosolizing.

Compositions of the invention may also be formulated as a substantially solid form. The term substantially solid means to encompass all solid forms, i.e. emulsions in solid form, gels, waxy solids, soapy solids, etc. In some embodiments, the composition may be in a form selected from a block, particles, flakes, beads, drops, spheres, or any other solid form. Within the context of the present disclosure, the term substantially solid is also meant to encompass carrier substrates at least partially coated with the solid compositions as disclosed herein; such as plastic beads or blocks coated with the solid compositions disclosed herein. Perforated substrates or foam structures carrying solid compositions disclosed herein within at least part of their perforations and/or foam pores are also contemplated within the scope of the present disclosure.

When in solid form, the at least one additive may be present in a content of between about 40 and 90 wt % of the composition. In other embodiments, the solid composition may comprise said at least one additive in a content of between about 40 and 85 wt %, between about 40 and 80 wt %, or even between about 40 and 75 wt % of the composition. In some other embodiments, the solid composition may comprise said at least one additive in a content of between about 45 and 90 wt %, between about 50 and 90 wt %, or even between about 55 and 90 wt % of the composition.

In some embodiments, the at least one additive is selected from selected from alkylphenol ethoxylates, fatty alcohols, alcohol ethoxylates, alcohol ethoxysulfates, polyoxyethylene glycol alkyl ethers, polyoxypropylene glycol alkyl ethers, glucoside alkyl ethers, glycerol alkyl esters polyoxyethylene glycol octylphenol ethers (Triton X-100), polyoxyethylene glycol sorbitan alkyl esters (polysorbate), sorbitan alkyl esters, cocamide MEA/DEA, block copolymers of polyethylene glycol and polypropylene glycol (poloxamers). In other embodiments, the at least on additive in the solid composition is $C_{14}$-$C_{18}$ alcohol ethoxylate.

According to some embodiments, said at least one additive is $C_{14}$-$C_{18}$ alcohol ethoxylate and said at least one eugenol-containing odor neutralizing agent is eugenol.

In order to obtain the desired viscosity and stabilize its solid form, the composition may further comprise at least one polyphosphate compound, which by some embodiments, may be present in a content of between 1 and 25% of the composition. In other embodiments, the at least one polyphosphate compound may be present in a content of between 4 and 25% of the composition. In some embodiments, the polyphosphate compound may be sodium triphosphate.

As noted above, the neutralization effect may be obtained by using relatively small quantities of the composition of the invention. The quantity of composition released into the liquid to be treated is determined by the dynamic solubility of the composition.

Thus, in some embodiments, the solid compositions of the invention have a controlled dynamic solubility in an aqueous phase to be treated in the range of between about 0.01 to 1 grams of the composition per 10 liters of said aqueous phase to be treated.

The term dynamic solubility relates to the solubility of a composition when exposed to a moving liquid phase, i.e. aqueous phase. Thus, the term denotes the solubility of the composition when a predetermined volume of liquid phase, e.g. 10 liter of water, is flown over the composition for a predetermined period of time (such as a few seconds).

In some embodiments, this period of time is in a range of between about 0.5 and 5 seconds. In other embodiments, the period of time may be in a range of about 1 and 2 seconds.

In some embodiments, the dynamic solubility of the composition is in the range of between about 0.01 to 0.5 grams of the composition per 10 liters of said aqueous phase to be treated when coming in contact with the composition for a period of time of between 0.5 to 5 seconds. In some embodiments, the dynamic solubility of the composition is in the range of between about 0.01 to 0.1 grams of the composition per 10 liters of said aqueous phase to be treated when coming in contact with the composition for a period of time of between 0.5 to 5 seconds.

According to some embodiments, the composition in solid form may comprise up to 15 wt % of water. In some embodiments, the solid composition comprises between about 5 and 15 wt % of water.

Compositions of the invention may further comprise additional components to render the composition with at least one other property, such as distinct odor, distinct color, etc. For this purpose, in some embodiments, the composition may further comprise at least one other additive selected from a perfume agent, coloring agent, a preservative, carrier oil, a water-soluble disinfecting agent and combinations thereof.

Another aspect of the invention provides an odor neutralizing composition comprising water, at least one eugenol-containing odor neutralizing agent, at least one emulsifier, at least one film-forming agent and at least one viscosity-controlling agent.

In a further aspect, the invention provides an odor neutralizing composition comprising water, at least one eugenol-containing odor neutralizing agent, at least one emulsifier, at least one film-forming agent and at least one viscosity-controlling agent, the composition having controlled dynamic solubility in an aqueous phase to be treated.

Another aspect of the invention provides a capsule comprising a water-dissolvable shell, the shell encapsulating a composition of the invention as herein described.

The invention also provides, in another of its aspects, a process for the manufacture of a composition comprising water, at least one eugenol-containing odor neutralizing agent, at least one emulsifier, at least one film-forming agent and at least one viscosity-controlling agent, the process comprising:

(a) mixing, at a first mixing speed, at least one odor neutralizing agent, at least one film-forming agent, and at least one viscosity-controlling agent to obtain a mixture;

(b) mixing, at a second speed, at least one emulsifier and water to obtain a solution; and (c) adding said solution into said mixture under mixing conditions permitting homogenization, to obtain a composition of the invention.

According to some embodiments, said mixing conditions are a mixing speed of between about 1,000 and 5,000 rpm (rotations per minute).

According to other embodiments, said first mixing speed being between about 5,000 and 15,000 rpm.

According to further embodiments, said second mixing speed being between about 5 and 25 rpm.

Mixing may be carried out by any type of suitable equipment known to a person of skill in the art, such as, but not limited to, pneumatic mixing paddles, electric mixing peddles, homogenizers, planetary mixers, sigma-blade mixers, rotating drum, etc.

In another aspect, the invention provides an odor neutralizing liquid composition comprising water, at least one eugenol-containing odor neutralizing agent, at least one film forming agent, and optionally at least one solvent.

In some embodiments, the eugenol-containing odor neutralizing agent in liquid form is selected from eugenol in pure form, at least one essential oil, and combinations thereof. The essential oil utilized in the liquid composition may be any one of the oils mentioned hereinabove.

In some embodiments, the odor neutralizing liquid composition comprises odor neutralizing agent content of between about 1 and 20 wt % of the composition.

When present in the liquid odor neutralizing composition of the invention, the at least one solvent may, in some embodiments, be a $C_{3-8}$ alcohol.

In some embodiments, the odor neutralizing liquid composition comprises a solvent content of between about 1 and 25 wt % of the composition.

In some other embodiments, the odor neutralizing liquid composition comprises water in a content of between about 50 and 90 wt % of the composition.

According to some embodiments, the odor neutralizing liquid composition comprises between about 1 and 30 wt % of the film forming agent, which may, by some embodiments, be MLO.

In some embodiments, the odor neutralizing liquid composition may further comprise at least one additive, which may be an emulsifier. The emulsifier may be present in the liquid composition in a content of between about 3 and 35 wt % of the composition.

According to some embodiments, the odor neutralizing liquid compositions of the invention is formulated for application by spraying or aerosolizing. Such formulation may be utilized for treating medium-to-large bodies of water, such as standing-water reservoirs, pools, ponds, bogs, sewage tanks, sewage-treating facilities, etc. Spraying or aerosolizing of the liquid compositions of the invention may be carried out by any conventional means known in the art, automated, semi-automated or manual.

Compositions of the invention may be further formulated for use in air-conditioning or ventilation systems for removing malodors from the air passing therethrough. In a non-limiting example, air to be treated may be passed through a filtering media comprising compositions of the invention to thereby remove malodors therefrom.

According to another aspect of the invention, there is provided substantially solid odor neutralizing composition comprising at least one eugenol-containing odor neutralizing agent, at least one film forming agent, and at least one additive.

In some embodiments, the eugenol-containing odor neutralizing agent is selected from eugenol, at least one essential oil, and combinations thereof, and may be present in a content of between about 1 and 20 wt % of the composition. In other embodiments, the at least one additive is selected from alkylphenol ethoxylates, fatty alcohols, alcohol ethoxylates, alcohol ethoxysulfates, polyoxyethylene glycol alkyl ethers, polyoxypropylene glycol alkyl ethers, glucoside alkyl ethers, glycerol alkyl esters polyoxyethylene glycol octylphenol ethers (Triton X-100), polyoxyethylene glycol sorbitan alkyl esters (polysorbate), sorbitan alkyl esters, cocamide MEA/DEA, block copolymers of polyethylene glycol and polypropylene glycol (poloxamers). In other embodiments, the at least one additive is $C_{14}$-$C_{18}$ alcohol ethoxylate, and may be optionally in a content of between about 40 and 90 wt % of the composition.

The solid odor neutralizing composition may further comprise at least one polyphosphate compound, which is some embodiments may be sodium triphosphate. According to some embodiment, the polyphosphate compound may be present in a content of between about 1 and 25 wt % of the composition.

In the solid odor neutralizing composition, said at least one film forming agent in a content of between about 1 and 20 wt %. The film-forming agent may, by some embodiments, be MLO.

According to some embodiments, the odor neutralizing solid composition may be characterized by a controlled dynamic solubility in an aqueous phase to be treated in the range of between about 0.01 to 1 grams of the composition per 10 liters of said aqueous phase to be treated.

According to another aspect of the invention, there is provided a composition as herein described for use in reducing concentration of volatile compounds in a gas phase.

In some embodiments, said volatile compounds are selected from sulfur-based volatile compounds, nitrogen-based volatile compounds, and mixtures thereof. Such volatile compounds may be, in accordance with some embodiments, selected from thiols, mercaptanes, $H_2S$, indoles (2,3-benzopyrrole), skatole (4-methyl-2,3-benzopyrrole), pyridines, pyrroles, and ammonia. As already mentioned herein, the composition of the invention physically encapsulates the volatile compounds, thereby reducing their volatility in the gas phase. The active component in the composition, i.e. the essential oil, may also chemically react with these compounds to further lower their volatility.

In another aspect, the invention provides a device for neutralizing odors, the device comprising a housing defining an internal space, the housing having at least one perforation and means for attachment to an applicable surface, the housing defining an internal space, and the internal space enclosing a composition as described herein.

In some embodiments, said means of attachment is selected from an adhesive, a hanging-ear, etc. Such attachment means allows a user to attach the device onto an internal surface of a water container to be treated, such as an internal surface of a toilet bowl.

In a further aspect of the invention, there is provided a method for reducing concentration of volatile compounds in a gas phase above an aqueous phase, the method comprising providing a composition according to the present invention, and contacting the composition with an aqueous phase to be treated.

In some embodiments, the contacting is carried out for a period of time allowing dissolution of between about 0.01 to 1 grams of the composition per 10 liters of aqueous phase. In other embodiments, the contacting is carried out for a period of time allowing dissolution of between about 0.01 to 0.5 grams of the composition per 10 liters of aqueous phase. In some other embodiments, the contacting is carried out for a period of time allowing dissolution of between about 0.01 to 0.1 grams of the composition per 10 liters of aqueous phase.

In accordance with some embodiments, said period of time is in a range of between about 0.5 and 5 seconds. In such embodiments, said period of time may be in a range of about 1 and 2 seconds.

In another aspect, the invention provides a method for reducing concentration of sulfur-based volatile compounds in a gas phase above an aqueous phase, the method comprising spraying a composition of the invention above an aqueous phase to be treated or into an environment to be treated.

DETAILED DESCRIPTION OF EMBODIMENTS

In order to better understand the subject matter that is disclosed herein and to exemplify how it may be carried out in practice, embodiments will now be described, by way of non-limiting example only.

EXAMPLE 1

Essential-oil Emulsion Compositions

Preparation of Compositions:
100 g batches of an exemplary composition of the invention were prepared by applying the following preparation method:
0.5-5 g of the viscosity-controlling agent Sepinov EMT-10 (hydroxyethyl-acrylate/sodium-acryloyldimethyltaurate copolymer) and MLO (mosquito lavicidal oil) ~10 g of MLO were added into clove-base essential oil and mixed by a Silverson homogenizer for 1 minute at 10,000 rpm to yield a viscous oily mixture. In a separate container, nonylphenol ethoxylate (NP10) emulsifier was mechanically mixed into water for about 2 minutes at 15 rpm, until a clear solution was obtained.

Then the solution was slowly added into the oily mixture while homogenizing at 3,000 rpm, resulting in a homogenous composition.

Dynamic Solubility Measurements

A perforated container was filled with the composition, and attached to a toilet bowl. The composition was exposed to several bowl rinses cycles, each releasing a water volume of approximately 10 liters. Differential weight measurements showed that the average dynamic solubility of the composition was about 0.3 g/10 liters of water.

Odor Elimination 0.03 g of the composition was solubilized into 1 liter of water (to mimic a concentration of 0.3 g/10 liters). 400 ml of this solution were placed in a glass container, into which 32 g of human solid feces were added, and the container was sealed. A control experiment comprised 32 g of human solid feces in clean water. Both containers were sealed for 15 minutes, and then the gas phase above the water was sampled and analyzed by gas chromatography. The results are provided in Table 1.

TABLE 1 odor elimination results for essential-oil emulsion compositions

| Volatile compound | Test sample | Control sample |
|---|---|---|
| Sulfides (as $H_2S$) | 2 ppm | 65 ppm |
| Mercaptanes | Below detection level | 2 ppm |
| Indole | Below detection level | Below detection level |
| Skatole | Below detection level | 2 ppm |

EXAMPLE 2

Eugenol Emulsion Compositions

Preparation of Compositions:

Batches of an exemplary composition of the invention were prepared by according to the method described in Example 1. The compositions are detailed in Table 2.

Viscosity was measured by using a Brookfield RVDV-I$^+$ viscometer, spindle 91 at a rotation speed of 20 RPM.

TABLE 2

Viscosity of eugenol emulsion compositions

| Comp. | Eugenol | MLO oil | EMT10 | NP10 | Water | Viscosity |
|---|---|---|---|---|---|---|
| Comp. 1 | 4.94 wt % | 9.88 wt % | 0.36 wt % | 5.73 wt % | 79 wt % | 220 cps |
| Comp. 2 | 4.93 wt % | 9.86 wt % | 0.69 wt % | 5.7 wt % | 78.82 wt % | 1450 cps |
| Comp. 3 | 4.9 wt % | 9.8 wt % | 1.37 wt % | 5.58 wt % | 78.35 wt % | 6230 cps |

EXAMPLE 3

Liquid Compositions

Preparation of Compositions:

Batches of an exemplary liquid composition of the invention were prepared by mixing 1-3 wt % of eugenol with 97-99 wt % of MLO oil.

Odor Elimination

The liquid composition having eguenol concentration of 2 wt % was sprayed over a 120 ml sample of sewage water placed in a glass container. A control experiment comprised 120 ml of raw sewage water. Both containers were sealed for 15 minutes, and then the gas phase above the water was sampled and analyzed by gas chromatography. The containers were then resealed and left in room temperature for 3 days, after which the gas phase above the water was drawn and analyzed. The results are provided in the Table 3.

TABLE 3 odor elimination results for eugenol liquid composition

| Volatile compound | Test sample | | Control sample | |
|---|---|---|---|---|
| | 15 min. | 3 days | 15 min. | 3 days |
| Sulfides (as $H_2S$) | Below detection level | 0.3 ppm | 12 ppm | 19 ppm |
| Mercaptanes | 0.3 ppm | 0.5 ppm | 9 ppm | 11 ppm |
| Indole | 0.1 ppm | 0.1 ppm | 5 ppm | 7 ppm |
| Skatole | Below detection level | | Below detection level | |

EXAMPLE 4

Aerosol Composition

Preparation of Compositions:

Batches of an exemplary composition of the invention were prepared by according to the method described in Example 1. The compositions are detailed in Table 4.

TABLE 4

Aerosolizable compositions

| Component | Wt % | Function |
|---|---|---|
| Water | Up to 70 | — |
| Nonylphenol ethoxylate (NP10) | 5-30 | Emulsifier |
| MLO | 5-25 | Film forming agent |
| Eugenol | 3-25 | Odor neutralizing agent |
| Perfume | 5-30 | Perfume |
| Isopropyl alcohol | 1-10 | Solvent |
| Simulgel INS 100 | 0.1-5 | Thickener |
| PEG-40 | 0.5-8.5 | Thickener/surfactant |
| Coloring agent | 0.001-1.0 | Coloring |

Odor Elimination

A liquid composition in accordance with Table 4 was sprayed over a sample of sewage water placed in a glass container. $H_2S$ presence above the liquid phase was measured by a Kitagawa AP-20 gas sampler equipped with $H_2S$-sensitive tube, in which $H_2S$ is reacted with lead acetate to form a visible change in coloration of the tube due to the formation of lead sulfate. The test tubes are suitable for detection of between 1 ppm and 300 ppm of $H_2S$ in a sample of 5-400 ml gas phase. A measurement of the gas phase above the sewage water sample prior to application of the liquid composition indicated presence of $H_2S$ above 1 ppm, as evident by the coloration of the tube. Then a liquid composition according to Table 4 was applied onto the surface of the sample by spraying, and the gas phase was tested again after several minutes using a new identical test tube. No coloration of the test tube was visible, attesting to reduction of the $H_2S$ in the gas phase below the threshold detection level of the tube.

EXAMPLE 5

Solid Composition

Preparation of Compositions:

100 g batches of an exemplary composition of the invention were prepared by applying the following preparation method:

MLO (mosquito lavicidal oil) was added into eugenol and mixed to homogenization. A mixture of $C_{16}$-$C_{18}$ alcohol ethoxylate and water was concomitantely prepared. The two mixtures were then thoroughly mixed. Perfume and coloring agents were then added, followed addition of sodium triphosphate. Then composition was mixed and then allowed to solidify.

The compositions are detailed in Table 5.

0.5-5 g of the viscosity-controlling agent Sepinov EMT-10 (hydroxyethyl-acrylate/sodium-acryloyldimethyltaurate copolymer) and MLO (mosquito lavicidal oil) ~10 g of MLO were added into clove-based essential oil and mixed by a Silverson homogenizer for 1 minute at 10,000 rpm to yield a viscous oily mixture. In a separate container, nonylphenol ethoxylate (NP10) emulsifier was mechanically mixed into water for about 2 minutes at 15 rpm, until a clear solution was obtained.

Then the solution was slowly added into the oily mixture while homogenizing at 3,000 rpm, resulting in a homogenous composition

TABLE 5

| Solid compositions | | |
|---|---|---|
| Component | Wt % | Function |
| $C_{16}$-$C_{18}$ alcohol ethoxylate | 40-90 | Emulsifier/carrier |
| Sodium triphosphate | 4-25 | Solidifier |
| MLO | 2-20 | Film forming agent |
| Eugenol | 2-15 | Odor neutralizing agent |
| Perfume | 1-10 | Perfume |
| Coloring agent | 0.1-3 | Coloring |
| Water | 5-15 | — |

Dynamic Solubility Measurements

A perforated container was filled with the composition, and attached to a toilet bowl. The composition was exposed to several bowl rinses cycles, each releasing a water volume of approximately 10 liters. Differential weight measurements showed that the average dynamic solubility of the composition was about 0.03-0.05 g/10 liters of water.

Odor Elimination $H_2S$ presence above a toilet bowl containing water and human solid feces was measured by a Kitagawa AP-20 gas sampler equipped with $H_2S$-sensitive tube, in which $H_2S$ is reacted with lead acetate to form a visible change in coloration of the tube due to the formation of lead sulfate. The test tubes are suitable for detection of between 1 ppm and 300 ppm of $H_2S$ in a sample of 5-400 ml gas phase. A measurement of the gas phase above the sample prior to application of the composition indicated presence of $H_2S$ above 1 ppm, as evident by the coloration of the tube.

Then, a solid composition according to Table 5 was attached to the inner side of the bowl, and the bowl was flushed with clean water to allow 0.03-0.05 g of the solid composition to dissolve and come into contact with the water in the bowl. The gas phase was tested again using a new identical test tube. No coloration of the test tube was visible, attesting to reduction of the $H_2S$ in the gas phase below the threshold detection level of the tube.

The invention claimed is:

1. An odor neutralizing composition comprising at least one eugenol-containing odor neutralizing agent and at least one film forming formulation, that comprises at least nonylphenol ethoxylate NP4, sorbitan oleate, silicon oil, hydrotreated light naphthenic paraffins and heavy paraffins.

2. The composition of claim 1, wherein said at least one eugenol containing odor neutralizing agent is selected from eugenol, at least one eugenol containing essential oil, and combinations thereof.

3. The composition of claim 1, wherein said at least one eugenol-containing odor neutralizing agent is present at a concentration of between about 1 and 20 wt % of the composition.

4. The composition of claim 1, wherein said film-forming formulation is present at a concentration of at least 1 wt % of the composition.

5. The composition of claim 1, further comprising at least one viscosity-controlling agent selected from acrylate/acrylomethyltaurate copolymers, hydroxylated acrylate/acrylomethyltaurate copolymers, polyacrylates, polyisobutenes, and polysorbates.

6. The composition of claim 5, wherein the at least one viscosity-controlling agent is present at a concentration of between about 0.5 and 1.5 wt % of the composition.

7. The composition of claim 1, further comprising at least one additive selected from the group consisting of alkylphenol ethoxylates, fatty alcohols, alcohol ethoxylates, alcohol ethoxysulfates, polyoxyethylene glycol alkyl ethers, polyoxypropylene glycol alkyl ethers, glucoside alkyl ethers, glycerol alkyl esters, polyoxyethylene glycol octylphenol ethers polyoxyethylene glycol sorbitan alkyl esters (polysorbate), sorbitan alkyl esters, cocamide monoethanolamine, cocamide diethanolamine, and block copolymers of polyethylene glycol and polypropylene glycol.

8. The composition of claim 1, being in a liquid form.

9. The composition of claim 1 further comprising at least one emulsifier, that is present at a concentration of between about 3 and 35 wt % of the composition.

10. The composition of claim 9, wherein said at least one emulsifier is nonylphenol ethoxylate NP10 and wherein said at least one eugenol-containing odor neutralizing agent is eugenol.

11. The composition of claim 9, wherein said composition has a viscosity of between about 200 and 6500 cps.

12. The composition of claim 1, being in a solid form.

13. The composition of claim 12, further comprising at least one additive that is present at a concentration of between about 40 and 90 wt % of the composition.

14. The composition of claim 13, wherein said at least one additive is C14-C18 alcohol ethoxylate and wherein said at least one eugenol-containing odor neutralizing agent is eugenol.

15. The composition of claim 12, having dynamic solubility in an aqueous phase to be treated in the range of between about 0.01 to 1 grams of the composition per 10 liters of said aqueous phase to be treated when coming in contact with the composition for a period of time between 0.5 to 5 seconds.

16. A composition of claim 1 formulated for reducing concentration of volatile compounds in a gas phase above an aqueous phase, or for reducing concentration of volatile compounds in a gas phase, the volatile compounds being selected from the group consisting of sulfur-based volatile compounds, nitrogen-based volatile compounds, and mixtures thereof.

17. A device for neutralizing odors in an aqueous phase, the device comprising a housing defining an internal space, the housing having at least one perforation and means for attachment to an applicable surface, the housing defining an internal space, and the internal space enclosing a composition according to claim 1.

\* \* \* \* \*